(12) United States Patent
Ames et al.

(10) Patent No.: US 7,026,338 B2
(45) Date of Patent: Apr. 11, 2006

(54) PHARMACEUTICAL NITRONES

(75) Inventors: Bruce N. Ames, Berkeley, CA (US);
Hani Atamna, Berkeley, CA (US)

(73) Assignee: Children's Hospital Research Center at Oakland, Oakland, CA (US)

( * ) Notice: Subject to any disclaimer, the term of this patent is extended or adjusted under 35 U.S.C. 154(b) by 26 days.

(21) Appl. No.: 10/843,167

(22) Filed: May 11, 2004

(65) Prior Publication Data

US 2005/0256088 A1 Nov. 17, 2005

(51) Int. Cl.
*C07D 213/02* (2006.01)
*A61K 31/44* (2006.01)
*A61K 31/395* (2006.01)

(52) U.S. Cl. ............ 514/345; 514/348; 514/410; 546/22; 546/290; 546/296; 548/416

(58) Field of Classification Search ........... 514/345, 514/348, 410; 546/22, 290, 296; 548/416
See application file for complete search history.

(56) References Cited

U.S. PATENT DOCUMENTS 6,455,589 B1 * 9/2002 Ames et al. .......... 514/645

* cited by examiner

*Primary Examiner*—Zinna Northington Davis
(74) *Attorney, Agent, or Firm*—Richard Aron Osman

(57) ABSTRACT

Pharmaceutical nitrone comprise condensates of an N-hydroxylamine and a physiological aldehyde, providing improved delivery and absorption, enhanced stability and reduced toxicity. Preferred physiological aldehydes are subject to endogenous cellular uptake transport, and include pyridoxal, pyridoxal phosphate, and heme-A. Essentially any physiologically compatible and pharmaceutically active hydroxylamine moiety may be incorporated, such as hydroxylamine moieties of prior pharmaceutical nitrones, and known pharmaceutically active hydroxylamines.

10 Claims, No Drawings

PHARMACEUTICAL NITRONES

FIELD OF THE INVENTION

The field of the invention is pharmaceutical nitrones of hydroxylamines and physiological aldehydes, such as pyridoxal.

BACKGROUND OF THE INVENTION

α-Phenyl-N-t-butyl nitrone (PBN) has been shown to reverse age-related oxidative changes, delay senescence, reverse mitochondrial decay, and exert a neuroprotective effect after oxidative damage from ischemia/reperfusion injury. In the course of studying the affect of PBN on cells we observed that old solutions were more effective than fresh solutions in delaying senescence. This observation led to our discovery of the anti-senescent effect of the PBN decomposition product, N-t-butyl hydroxylamine in particular, and N-hydroxylamines in general; see our U.S. Pat. No.6,455,589.

Our findings indicate that pharmaceutical nitrones can act as prodrugs, liberating the more biologically active hydroxylamine under physiological conditions. The present invention provides pharmaceutical nitrones of hydroxylamines and physiologically-preferred aldehydes.

SUMMARY OF THE INVENTION

The invention provides compositions comprising a nitrone of an N-hydroxylamine and a physiological aldehyde, and related methods, including therapy and manufacture. The subject compositions include a pharmaceutical compositions comprising a nitrone of an N-hydroxylamine and a physiological aldehyde, such as pyridoxal (PXAL; Vitamin B6), pyridoxal phosphate (PLP), and heme-A, or a pharmaceutical salt thereof; and a pharmaceutically acceptable excipient. Preferred N-hydroxylamines are primary N-hydroxylamine, and numerous, diverse examples are provided below. The compositions may be provided in orally administrable effective unit dosages, and/or may be copackaged with a label identifying the N-hydroxylamine and prescribing a pharmaceutical use thereof, particularly wherein the use comprises reducing oxidative damage or delaying senescence.

The invention also provides methods of making the subject compositions, particulary methods comprising condensing the hydroxylamine and the aldehyde to form the nitrone. The invention also provides methods of using the subject compositions, particularly methods comprising administering or prescribing the composition to a patient determined to be in need thereof, and optionally detecting a resultant therapeutic improvement, particularly a reduction in oxidative damage or delay of senescence in the patient.

DETAILED DESCRIPTION OF PARTICULAR EMBODIMENTS OF THE INVENTION

The invention provides compositions comprising a nitrone of an N-hydroxylamine and a physiological aldehyde, and related methods, including therapy and manufacture. By incorporating a physiological aldehyde, the subject nitrones can provide a variety of improvements, including improved delivery and absorption, enhanced stability and reduced toxicity, as compared with corresponding nitrones incorporating non-physiological aldehydes, such as benzaldehyde. Preferred physiological aldehydes are subject to endogenous cellular uptake transport which facilitates delivery. The physiological aldehyde moiety is derived from natural physiological aldehydes such as pyridoxal (PXAL; Vitamin B6), pyridoxal phosphate (PLP), and heme-A.

Essentially any physiologically compatible and pharmaceutically active N-hydroxylamine moiety may be incorporated, such as N-hydroxylamine moieties of prior pharmaceutical nitrones, and known pharmaceutically active hydroxylamines. Exemplary hydroxylamine moieties which may be incorporated in the subject nitrones are found in the prior art nitrones of U.S. Pat. Nos. 6,197,826; 6,310,092; 3,376,540; 6,255,353; 6,342,523; 6,441,032; 6,433,008; 6,509,378; 6,486,349; 6,258,852; 6,083,989; and 6,545,056; and Publ Nos. US2003/0078297 and US2002/0165274. In particular embodiments, the hydroxylamine is a primary N-hydroxylamine, such as described in U.S. Pat. No.6,455,589.

In particular embodiments, the composition is a pharmaceutical composition comprising the nitrone and a pharmaceutically acceptable excipient, which may be provided in an orally administrable effective unit dosage. The subject compositions may be administered in various forms, formulations and routes using standard materials and protocols; see, e.g. Remington's Pharmaceutical Sciences. The compositions may be packaged with a label identifying the N-hydroxylamine and prescribing a pharmaceutical use thereof, such as reducing oxidative damage or delaying senescence.

The invention also provides methods of making the subject compositions, e.g. by condensing the hydroxylamine and the aldehyde to form the nitrone. Exemplary condensation reaction conditions are shown in Scheme 4 of Durand et al., J. Med. Chem. 2003, 46, 5230–5237. The N-hydroxylamine moiety is typically prepared by oxidizing the corresponding amine; see, e.g. U.S. Pat. No.6,455,589; Durand et al., J. Med. Chem. 2003, 46, 5230–5237, and citations therein.

The invention also provides methods of using the subject compositions, e.g. by administering or prescribing the composition to a patient determined to be in need thereof, and optionally detecting a resultant reduction in oxidative damage or delay of senescence in the patient.

In one embodiment, the subject nitrone if formed by reacting of pyridoxal (PXAL; Vitamin B6) or pyridoxal phosphate (PLP) (the coenzyme that vitamin B6 is converted to in the cell ) with a hydroxylamine, such as NtBHA (Schematics 1 & 2). Another exemplary physiological aldehyde useful for forming the subject condensation products with hydroxylamines is the aromatic aldehyde containing heme-A (Schematic 3), a prosthetic group of cytochrome C oxidase (COX) and which is synthesized and utilized in mitochondria.

Schematics 1, 2.

Nitrone of NtBHA¹ + Pyridoxal

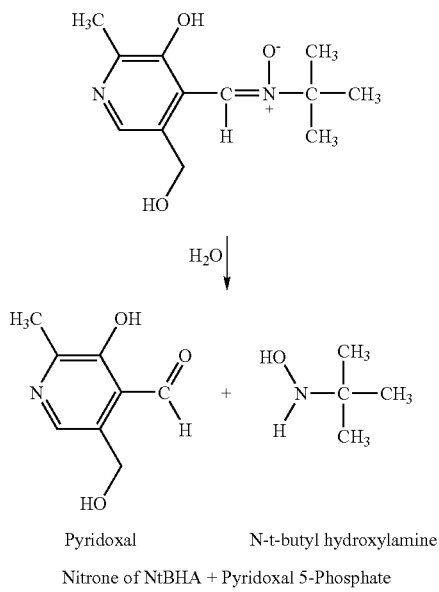

Nitrone of NtBHA + Pyridoxal 5-Phosphate

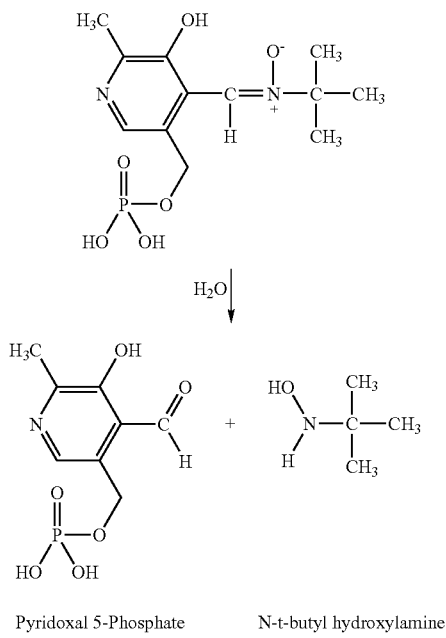

1NtBHA; N-t-Butyl hydroxylamine.

Schematic 3.

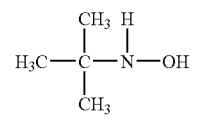

N-t-Butyl hydroxylamine
(NtBHA)

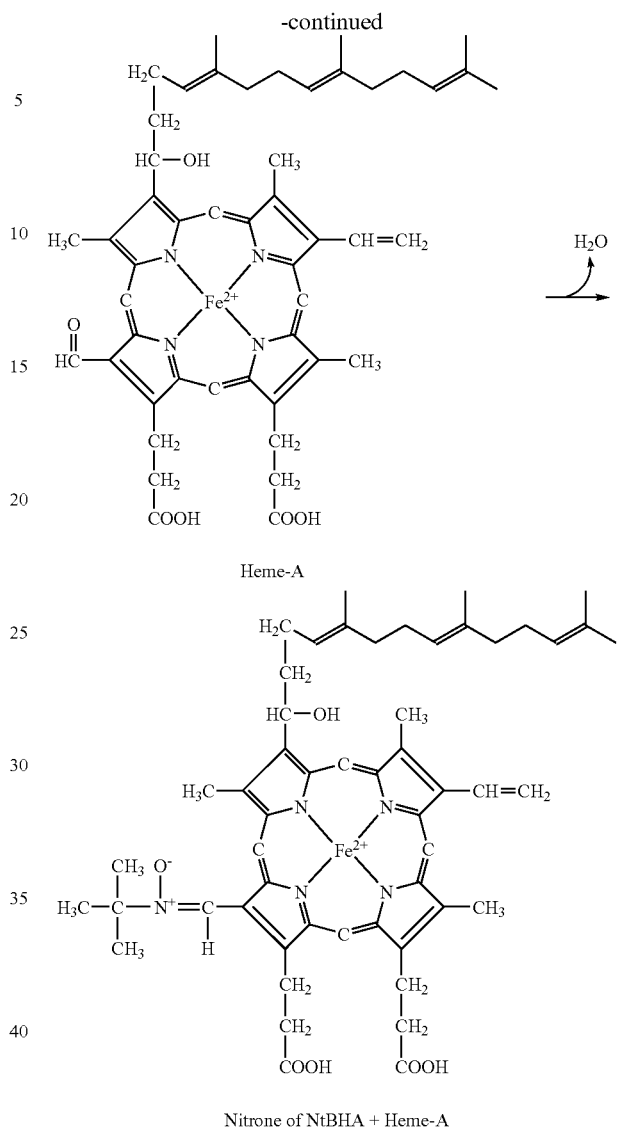

Applications

As therapeutics and/or prophylactics, the nitrones of this invention are useful for treating a wide variety of medical dysfunctions and diseases, particularly in human patients. Among the various medical conditions which may be prevented and/or treated, the subject nitrones are particularly useful for treating conditions involving acute oxidate damage, such as acute intense oxidative damage to a region of the central nervous system, e.g. stroke, conditions associated with stroke, concussion and subarachnoid hemorrhage or chronic oxidate damage, such as is associated with senescence and aging. Accordingly, the subject compositions are useful in treating a variety of dysfunctions or disorders characterized by oxidized proteins, nucleic acids or lipids in the tissues, cells, or associated fluids (such as the blood). Cellular, tissue, systemic and organismal indicia of oxidative damage are known in the art and exemplified below; for example, in vitro cellular oxidative damage and senescence may be measured as described in Chen et al. (1995) Proc. Natl. Acad. Sci. USA 92, 4337–4341.

Applicable target disorders are generally divided into disorders of the central and peripheral nervous system and disorders of the peripheral organs. Disorders of the CNS include stroke, aging, neurodegenerative conditions, such as Alzheimer's disease, Parkinsonism, concussion, aneurysm, ventricular hemorrhage and associated vasospasm, migraine and other vascular headaches, spinal cord trauma, neuroanesthesia adjunct, HIV-dementia and the like. Disorders of the peripheral nervous system include diabetic peripheral neuropathy and traumatic nerve damage. Peripheral organ disease includes atherosclerosis (both diabetic and spontaneous), chronic obstructive pulmonary disease (COPD), pancreatitis, pulmonary fibrosis due to chemotherapeutic agents, angioplasty, trauma, burns, ischemic bowel disease, wounds, ulcers and bed sores, lupus, ulcerative colitis, organ transplantation, renal hypertension, overexertion of skeletal muscle, epistaxis (pulmonary bleeding), autoimmune conditions, such as systemic lupus (erythematosus), multiple sclerosis and the like; and inflammatory conditions, such as inflammatory bowel disease, rheumatoid arthritis, septic shock, erythema nodosum leprosy, septicemia, uveitis, and the like. Some disease conditions may be classified as, for example, both autoimmune and inflammatory conditions, such as multiple sclerosis and the like.

Other conditions associated: with excessive oxidation of proteins or lipids that can be treated include undesirable or altered oxidation of low density lipoprotein; and dysfunction from exposure to radiation, including x-ray, ultraviolet, gamma and beta radiation, and cytotoxic compounds, including those used for chemotherapy for cancer and viral infections.

Accordingly, in one aspect, the invention provides a method for treating a patient with an acute central nervous system disorder, said method comprising administering to said patient a pharmaceutical composition comprising a pharmaceutically acceptable carrier and an effective acute central nervous system disorder-treating subject nitrone. In a preferred embodiment of this method, the acute central nervous system disorder treated is stroke.

In another aspect, the invention provides a method for treating a patient with an acute cardiovascular disorder, said method comprising administering to said patient a pharmaceutical composition comprising a pharmaceutically acceptable carrier and an effective acute cardiovascular disorder-treating amount of a subject nitrone. In a preferred embodiment of this method, the acute cardiovascular disorder treated is cardiac infarction.

In still another aspect, the invention is directed to a method for treating a patient with a neurodegenerative disease which method comprises administering to said patient a pharmaceutical composition comprising a pharmaceutically acceptable carrier and an effective neurodegenerative disease-treating amount of a subject nitrone. Additionally, the invention is directed to a method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a subject nitrone. In preferred embodiments of this invention, the neurodegenerative disease treated and/or prevented in the above methods is Alzheimer's disease, Parkinson's disease, HIV dementia, a dopamine-associated neurodegenerative condition and the like.

In yet another aspect, the invention is directed to a method for treating a patient with an autoimmune disease which method comprises administering to said patient a pharmaceutical composition comprising a pharmaceutically acceptable carrier and an effective autoimmune disease-treating amount of a subject nitrone. The invention is also directed to a method for preventing the onset of an autoimmune disease in a patient at risk for developing the autoimmune disease which method comprises administering to said patient a pharmaceutical composition comprising a pharmaceutically acceptable carrier and an effective autoimmune disease-preventing amount of a subject nitrone. In preferred embodiments of this invention, the autoimmune disease treated and/or prevented in the above methods is systemic lupus, multiple sclerosis and the like.

In still another aspect, the invention is directed to a method for treating a patient with an inflammatory disease which method comprises administering to said patient a pharmaceutical composition comprising a pharmaceutically acceptable carrier and an effective inflammatory disease-treating amount of a subject nitrone. Additionally, the invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a subject nitrone. In preferred embodiments of this invention, the inflammatory disease treated and/or prevented in the above methods is rheumatoid arthritis, septic shock, erythema nodosum leprosy, septicemia, uveitis and the like.

In another aspect the invention provides a method for treating a patient suffering from a condition characterized by progressive loss of nervous system function due to mitochondrial dysfunction. This method involves administering to the patient with loss of central nervous system function an effective amount of one or more of the pharmaceutical compositions described herein.

In each aspect, the invention may be implemented by a first diagnostic step, e.g. determining that the patient is suffering from, subject to, or predisposed to a target disease or condition followed by prescribing and/or administering to the patient a subject nitrone composition, optionally followed by a evaluation/confirmation/prognosis step, e.g. determining an effect of the treatment, such as an amelioration of symptom of a targeted disease or condition or an indicator thereof.

Administration

The subject compositions may be formulated for administration by any route, including without limitation, oral, buccal, sublingual, rectal, parenteral, topical, inhalational, including itnranasal, injectable, including subcutaneous, intravenous, intramuscular, etc., topical, including transdermal, etc. The subject compositions are administered in a pharmaceutically (including therapeutically, prophylactically and diagnostically) effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

Intravenous dose levels for treating acute medical conditions range from about 0.1 mg/kg/hour to at least 10 mg/kg/hour over a period of from about 1 to about 120 hours and especially 24 to 96 hours. Preferably, an amount of at least about 0.2 mg/kg/hour is administered to the patient. A preloading bolus of from about 10 mg to about 500 mg may also be administered to achieve adequate steady state levels. While intravenous administration is preferred for acute treatments, other forms of parenteral administration, such as intramuscular injection can be used, as well. In such cases, dose levels similar to those described above may be employed.

Another acute condition which can be advantageously treated with the nitrones of this invention is acute oxidative damage to the cardiovascular system, such as the damage which occurs in a patient who has suffered a cardiac infarction or the like. When treating such a condition, a pharmaceutical composition comprising a subject nitrone is administered parenterally, e.g. intravenously, at doses similar to those described above for stroke and other acute CNS conditions.

As discussed above, the compounds described herein are suitable for use in a variety of drug delivery systems. Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.02 to about 50 mg/kg of nitrone, with preferred doses each providing from about 0.04 to about 30 mg/kg and especially about 1 to about 10 mg/kg.

When used to prevent the onset of a degenerative condition, such as a neurodegenerative, autoimmune or inflammatory condition, the nitrone compositions of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition. When used prophylactically, the subject pharmaceutical compositions are administered orally to the predisposed patient. The doses for this oral therapy will typically be derived from those set forth above for treating persons suffering from the neurodegenerative, autoimmune or inflammatory condition.

The compounds of this invention can be administered as the sole active agent or they can be administered in combination with other agents, including other active nitrones or hydroxylamine compounds.

EXAMPLES

The following formulation examples illustrate representative pharmaceutical compositions of this invention. The present invention, however, is not limited to the following exemplified pharmaceutical compositions.

Formulation 1—Tablets: The nitrone of NtBHA and pyridoxal is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 2—Tablets: The nitrone of N-benzylhydroxylamine and pyridoxal is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 3—Capsules: The nitrone of N-(n-nitrobenzyl)hydroxylamine and pyridoxal 5-phosphate is admixed as a dry powder with a starch diluent in an approximate 1:1 weight ratio. The mixture is filled into 250 mg capsules (125 mg of active nitrone compound per capsule).

Formulation 4—Capsules: The nitrone of N-(hydroxymethyl)hydroxylamine and pyridoxal 5-phosphate is admixed as a dry powder with a starch diluent in an approximate 1:1 weight ratio. The mixture is filled into 250 mg capsules (125 mg of active nitrone compound per capsule).

Formulation 5—Liquid: The nitrone of N-(acetyloxymethyl)hydroxylamine and Heme-A (50 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 6—Liquid: The nitrone of N-aminomethylhydroxylamine and Heme-A (50 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 7—Injection: The nitrone of 1-hydroxylamine-butane-4-sulfonic acid and pyridoxal is dissolved in a buffered sterile saline injectable aqueous medium to a concentration of approximately 5 mg/ml.

Formulation 8—Injection: The nitrone of N-(2-nitroethyl)hydroxylamine and pyridoxal is dissolved in a buffered sterile saline injectable aqueous medium to a concentration of approximately 5 mg/ml.

The foregoing detailed description and examples are offered to illustrate this invention and are not to be construed in any way as limiting the scope of this invention.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutical composition comprising a nitrone of an N-hydroxylamine and a physiological aldehyde selected from the group consisting of: pyridoxal, pyridoxal phosphate, and heme-A, or a pharmaceutical salt thereof, and a pharmaceutically acceptable excipient.

2. The composition of claim 1, wherein the aldehyde is pyridoxal.

3. The composition of claim 1, wherein the aldehyde is pyridoxal phosphate.

4. The composition of claim 1, wherein the aldehyde is heme-A.

5. The composition of claim 1, in an orally administrable effective unit dosage.

6. The composition of claim 1, wherein the N-hydroxylamine is a primary N-hydroxylamine.

7. The composition of claim 1 packaged with a label identifying the N-hydroxylamine and prescribing a pharmaceutical use thereof, wherein the use comprises reducing oxidative damage or delaying senescence.

8. A method of making the composition of claim 1, the method comprising condensing the hydroxylamine and the aldehyde to form the nitrone.

9. A method of using the composition of claim 1, the method comprising administering or prescribing the composition to a patient determined to be in need thereof.

10. A method of using the composition of claim 1, the method comprising administering or prescribing the composition to a patient determined to be in need thereof, and detecting a resultant reduction in oxidative damage or delay of senescence in the patient.

* * * * *